(12) United States Patent
van Schriek et al.

(10) Patent No.: US 11,360,068 B2
(45) Date of Patent: Jun. 14, 2022

(54) MONITORING PLANTS

(71) Applicant: Keygene N.V., Wageningen (NL)

(72) Inventors: Marco Gerardus Maria van Schriek, Wageningen (NL); Rudolf Laurentius van Bavel, Wageningen (NL)

(73) Assignee: Keygene N V., Wageningen (NL)

( * ) Notice: Subject to any disclaimer, the term of this patent is extended or adjusted under 35 U.S.C. 154(b) by 202 days.

(21) Appl. No.: 16/476,906

(22) PCT Filed: Jan. 11, 2018

(86) PCT No.: PCT/EP2018/050638
§ 371 (c)(1),
(2) Date: Jul. 10, 2019

(87) PCT Pub. No.: WO2018/130606
PCT Pub. Date: Jul. 19, 2018

(65) Prior Publication Data
US 2020/0003743 A1     Jan. 2, 2020

(30) Foreign Application Priority Data
Jan. 16, 2017   (EP) .................................... 17151662

(51) Int. Cl.
*G01N 33/00* (2006.01)
*G06T 19/00* (2011.01)

(52) U.S. Cl.
CPC ......... *G01N 33/0098* (2013.01); *G06T 19/00* (2013.01)

(58) Field of Classification Search
CPC ... G01N 33/0098; G06T 19/00; G06T 11/001; G06T 15/04; G06T 15/10; G06T 2210/52;
(Continued)

(56) References Cited

U.S. PATENT DOCUMENTS

| 9,002,071 B2 * | 4/2015 | Nakagome | ......... G06K 9/00657 |
| | | | 382/110 |
| 2006/0224327 A1 * | 10/2006 | Dunlap | .................. G06Q 30/02 |
| | | | 702/19 |

(Continued)

FOREIGN PATENT DOCUMENTS

WO     2013024364     2/2013

OTHER PUBLICATIONS

Dawei Li et al: "Digitization and Visualization of Greenhouse Tomato Plants in Indoor Environments", Sensors, vol. 15, No. 2, Feb. 10, 2015.

(Continued)

*Primary Examiner* — Abderrahim Merouan
(74) *Attorney, Agent, or Firm* — N.V. Nederlandsch Octrooibureau

(57) ABSTRACT

A system for monitoring plants comprises an input unit, an output unit, and a processor that provides (201) image data (107) for a plurality of plants, each image data being associated with an individual plant. It associates (204) the image data (107) of each plant with corresponding plant characteristic data (109). It selects (206) a subset of the plants based on the plant characteristic data (109). It generates (207) a plurality of computer graphics objects corresponding to the selected plants. It applies (208) the image data (107) of each selected plant in form of a computer graphics texture to the corresponding computer graphics object. It determines (209) a position of each computer graphics object in a three-dimensional space of a computer graphics scene. It creates (210) a computer graphics rendering of the scene. It displays (211) the computer graphics rendering.

15 Claims, 8 Drawing Sheets

(58) Field of Classification Search
CPC ....... G06T 15/80; G06T 17/20; G06T 19/006;
G06T 19/20; G06T 2219/2008; G06T
2219/2016; G06T 2219/2021; G06T 7/20;
G06Q 30/02; G06K 9/00624; G06K 9/46;
G06K 9/527
See application file for complete search history.

(56) References Cited

U.S. PATENT DOCUMENTS

| | | | |
|---|---|---|---|
| 2014/0154729 A1* | 6/2014 | Leyns | G01N 21/17 435/29 |
| 2014/0184585 A1* | 7/2014 | Unger | G06T 9/00 345/419 |
| 2014/0337764 A1* | 11/2014 | Caraballoso | G06F 30/13 715/753 |
| 2014/0344013 A1* | 11/2014 | Karty | G06Q 30/0201 705/7.29 |
| 2015/0035830 A1* | 2/2015 | Zhang | G06T 15/10 345/426 |
| 2015/0325038 A1* | 11/2015 | Baker | G06Q 30/0643 345/426 |
| 2017/0071188 A1* | 3/2017 | Rees | G06K 9/52 |
| 2017/0286772 A1* | 10/2017 | Workman | H04L 67/10 |
| 2020/0003743 A1* | 1/2020 | van Schriek | G06T 19/00 |
| 2020/0126239 A1* | 4/2020 | Qian | B64D 47/08 |
| 2020/0279374 A1* | 9/2020 | King | G06K 9/00697 |

OTHER PUBLICATIONS

M. P. Pound et al: "Automated Recovery of Three-Dimensional Models of Plant Shoots from Multiple Color Images", Plant Physiology, vol. 166, No. 4, Oct. 20, 2014.

N Sigrimis: "New Ways on Supervisory Control of a Virtual Greenhouse to Train and to Manage", Jan. 1, 2000 (Jan. 1, 2000), Retrieved from the Internet: URL:http://ac.els-cdn.com/S1474667017367459/1-S2.0-S1474667017367459-main.pdf?_tid=f3920ba2-5cdb-Ile7-ad6c-00000aacb360&acdnat=1498748721 beeb5bb57c364cbfacaf6205b442f396 [retrieved on Jun. 29, 2017].

* cited by examiner

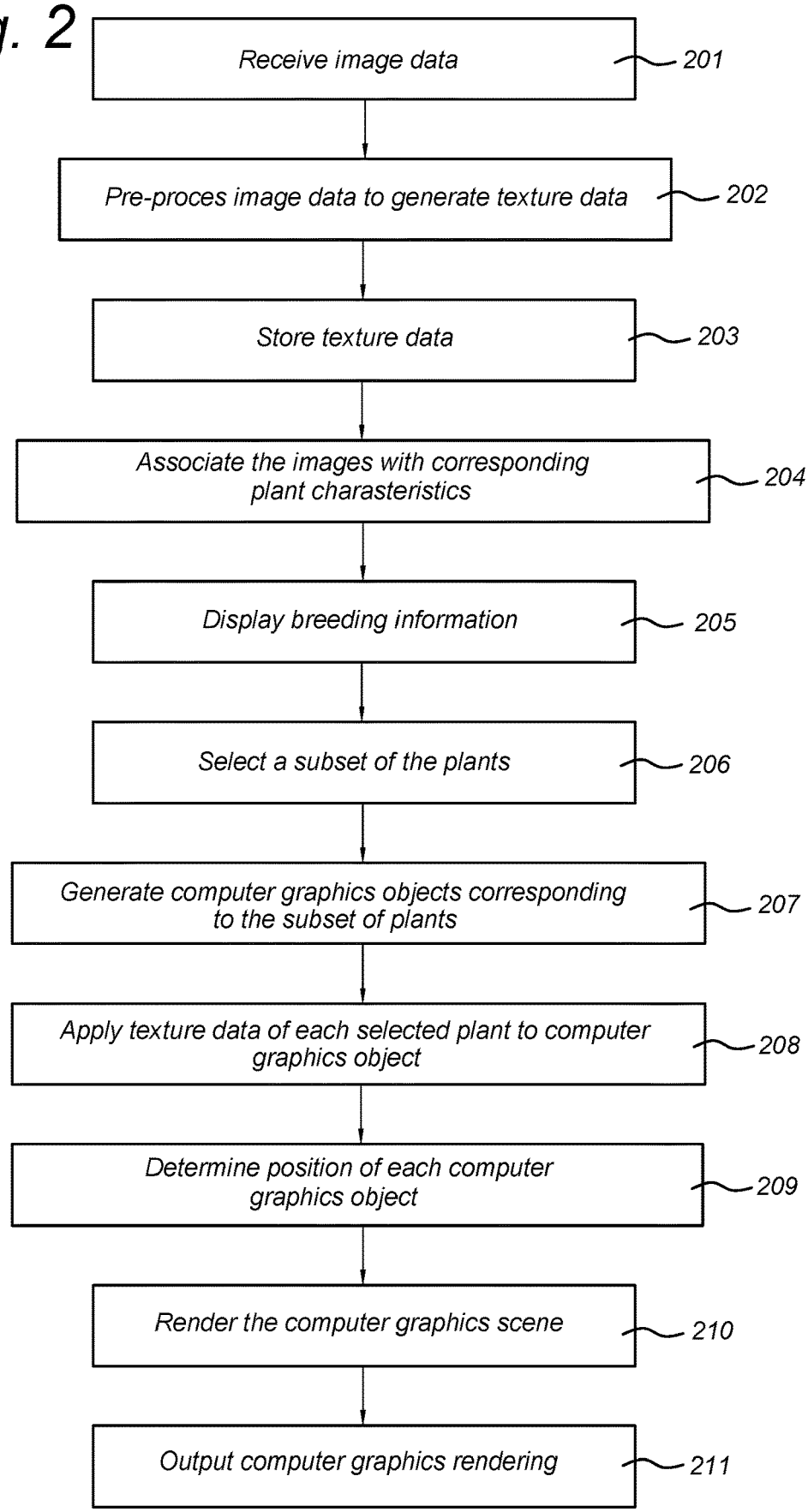

MONITORING PLANTS

FIELD OF THE INVENTION

The invention relates to monitoring plants.

BACKGROUND OF THE INVENTION

The total amount of information available for a breeder to steer his or her breeding program is overwhelming. Several statistical analyses may be performed regarding certain observed phenotypes of certain plants. Also, visual inspection of the plants may be performed by a breeding specialist. An apparatus for automated systematic photographing of plants during the breeding process is known to exist. However, this apparatus further increases the amount of data that becomes available to the breeder, making it challenging to involve the available data fully in the breeding decisions.

SUMMARY OF THE INVENTION

An object of the invention is to provide an improved system for monitoring plants, in particular plants in a breeding program.

According to an aspect of the invention, a system for monitoring plants is provided. The system comprises
an input unit for receiving image data;
a processor configured to control:
providing image data for a plurality of plants, each image data being associated with an individual plant;
associating the image data of each plant with corresponding plant characteristic data,
selecting a subset of the plants based on the plant characteristic data,
generating a plurality of computer graphics objects corresponding to the selected plants,
applying the image data of each selected plant in form of a computer graphics texture to the corresponding computer graphics object,
determining a position of each computer graphics object in a three-dimensional space of a computer graphics scene, and
creating a computer graphics rendering of the scene; and
an output unit for displaying the computer graphics rendering.

This provides improved visualizations of the available image data, because the selected plants are given three-dimensional positions, making it possible to create a virtual greenhouse filled with the available species. The three-dimensional rendering makes it possible to focus on particular ones of the species (nearby), while still providing the overview over the other selected species (further away). This technique helps the breeder to find desirable features in plants more easily.

For example, the plant characteristic information of a plant comprises information about at least one of a phenotype of the plant, a genotype of the plant, a stage of development of the plant, and an experimental condition to which the plant was exposed.

The processor may be further configured to control selecting at least one filter option based on a user input, wherein the at least one filter option defines a filter with respect to the plant characteristic data; wherein the selecting the subset of the plants is further based on the filter option. This allows to select the plants that will be present in the three-dimensional space based on appropriate filters. Thus, different plants having certain characteristics are put side-by-side in a virtual world for expert evaluation.

The determining a position of each computer graphics object may comprise determining a position of each computer graphics object based on the plant characteristics information. The position based on this information allows to display plants that have closely related features spatially close to each other. This may facilitate review of the plant characteristics.

The processor may be further configured to control selecting at least one sorting option based on a user input, wherein the at least one sorting option defines an order of the plants with respect to the plant characteristic information, wherein the three-dimensional position of each computer graphics object is further based on the defined order of the plants. This allows the user to quickly re-arrange the visualization by changing the sorting option, which will change the three-dimensional positions of the plants in the computer graphics scene.

The processor may be configured to control providing pre-processed computer graphics texture data for each of the plurality of plants before selecting the subset of the plants, wherein the computer graphics texture data is in a texture compressed form. This way, different selections can quickly be made on the spot and displayed without delay.

The pre-processing step of converting the image data into the computer graphics texture data associated with each plant may comprise generating a plurality of versions of the texture at different scales. This facilitates the quick display of the plants, in particular if the number of images and plants is large. It may enhance 'real-time' display of any selection of the available plants and images.

The image data may comprise a plurality of photographs of an individual plant taken from a plurality of different viewing angles. The computer graphics objects may have faces corresponding to the plurality of different viewing angles. The texture data corresponding to a photographic image may be applied to the corresponding face of the computer graphics object. This way, visualization of the available photographic data is made particularly efficient. It is not necessary to generate a detailed three-dimensional model of the shape of each plant.

The creating a computer graphics rendering may comprise creating a stereoscopic computer graphics rendering for a binocular viewing device. This facilitates creating a virtual reality experience of the plant data.

The system may further comprise a user interface device for receiving a user input. The processor may further be configured to control adapting a viewing position or a viewing direction of the observer, the viewing position or viewing direction being used for the creating the computer graphics rendering, based on the user input received through the user interface device. This allows to create a real-time, live virtual walk through the computer graphic scene, enabling the user to view the displayed plants from any desired position.

The processor may be further configured to control exchanging information about the selection of the subset of the plants with a server or another system for monitoring plants, and synchronizing the selection of the plants and the three-dimensional positions of the computer graphic objects with the server or the other system for monitoring plants. This allows to share a particular three-dimensional visualization of a selection of the plants with another user, who may be located at a different location.

The processor may be further configured to control transmitting and receiving information about the viewing position or viewing direction used for creating the computer graphics rendering with the server or the other system for monitoring plants, and creating a computer graphics object representing another user and assigning a position to the computer graphic object representing the other user in the computer graphics scene based on the received information about the viewing position or viewing direction of the other user, and including the computer graphics object representing the other user in the computer graphics rendering of the scene. This allows the users, who may be located remote from each other, to see what the other users are looking at or evaluating. It may also allow the users to see what the other user is pointing at. Also, a user may highlight some portion of the scene, which highlighting may be made visible to all other users.

The displaying breeding information including statistics of plant characteristic data, such as of the phenotype information or genotype information, may comprise generating a computer graphics object representing the breeding information, associating it with a position in the computer graphics scene, and including the computer graphics object representing the breeding information in the computer graphics rendering of the scene. This allows, for example in a VR environment, to view the breeding information inside the VR environment, without leaving the VR environment.

The processor may be configured to control retrieving the breeding information to be displayed from a server program by submitting a request to an application program interface of the server program, wherein the request is indicative of at least one filter option and/or sorting option with respect to the plant characteristic data, wherein the selecting the subset of the plants is performed based on the filter option indicated by the request or the determining the position of each computer graphics object is performed based on the sorting option indicated by the request. This way, the computer graphics objects may be automatically made consistent with the displayed breeding information.

According to another aspect of the invention, a method of monitoring plants is provided, comprising
providing image data for a plurality of plants, each image data being associated with an individual plant;
associating the image data of each plant with corresponding plant characteristic data;
selecting a subset of the plants based on the plant characteristic data,
generating a plurality of computer graphics objects corresponding to the selected plants;
applying the image data of each selected plant in form of a computer graphics texture to the corresponding computer graphics object;
determining a position of each computer graphics object in a three-dimensional space of a computer graphics scene;
creating a computer graphics rendering of the scene; and
displaying the computer graphics rendering.

According to another aspect of the invention, a computer program product is provided, comprising instructions for causing a computer system to perform the method set forth.

The person skilled in the art will understand that the features described above may be combined in any way deemed useful. Moreover, modifications and variations described in respect of the system may likewise be applied to the method and to the computer program product, and modifications and variations described in respect of the method may likewise be applied to the system and to the computer program product.

BRIEF DESCRIPTION OF THE DRAWINGS

In the following, aspects of the invention will be elucidated by means of examples, with reference to the drawings. The drawings are diagrammatic and may not be drawn to scale. Throughout the drawings, similar items may be marked with the same reference numeral.

FIG. 2 shows a flowchart of a method for monitoring plants.

DETAILED DESCRIPTION OF EMBODIMENTS

Certain exemplary embodiments will be described in greater detail, with reference to the accompanying drawings.

The matters disclosed in the description, such as detailed construction and elements, are provided to assist in a comprehensive understanding of the exemplary embodiments. Accordingly, it is apparent that the exemplary embodiments can be carried out without those specifically defined matters. Also, well-known operations or structures are not described in detail, since they would obscure the description with unnecessary detail.

Figure 1:
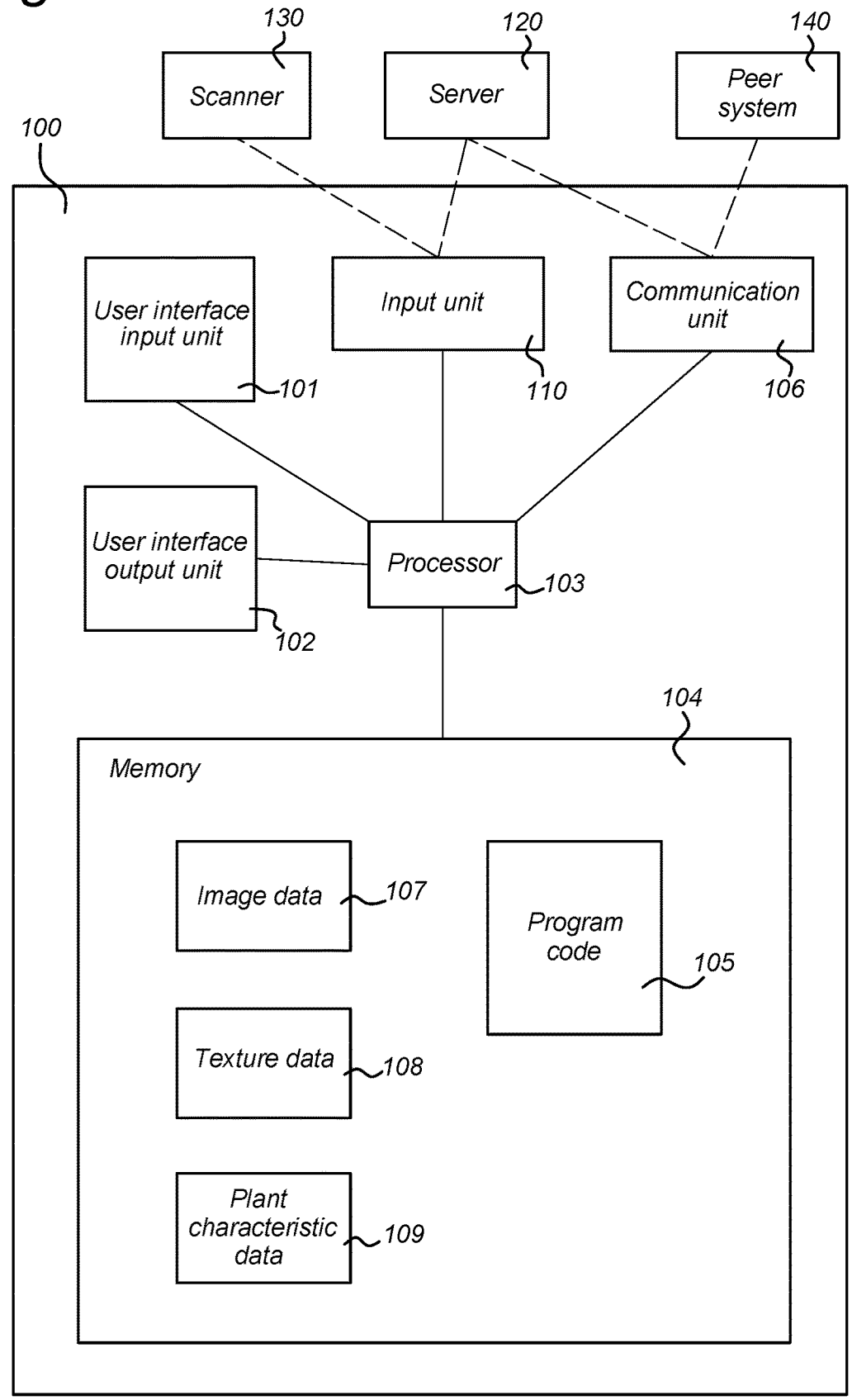
FIG. 1 shows a block diagram of a system for monitoring plants.

FIG. 1 illustrates an example implementation of a system 100 for monitoring plants. The system may be a computer system for example. The system may operate in cooperation with a scanning device (not shown), that is capable of scanning large amounts of plants individually. This scanning device may be configured to take photographs of each plant from different viewing directions. Separate photographs may be taken of the plant and its roots. Alternatively, the scanning device may be configured to make other types of scans than photographs, for example X-ray based scans or three-dimensional scans. The scan data is stored on a data storage and retrieval system, tentatively illustrated as server 120 in the drawing. The server 120 may be connected to a communication unit 106 of the system 100. The communication unit may comprise a communication port, such as an ethernet connector or a USB connector, to connect to the server. The connection between the server 120 and the communication unit 106 of the system 100 may be via a wired or wireless connection and may be via a network connection, such as an Internet connection. In an alternative implementation, the server 120 and the system 100 may be integrated in a single device, and the communication unit 106 may be an internal communication bus within the single device. The system may further comprise a user interface input unit 101, a user interface output unit 102, a processor 103, a memory 104, a communication unit 106, and an input unit 110.

The user interface input unit 101 may comprise any user interface device such as a keyboard, mouse, or a virtual reality controller, which virtual reality controller be configured to detect haptic feedback, for example by means of a gyro sensor. In addition or alternatively the virtual reality controller may comprise control buttons that a user can press to give commands.

The user interface output unit 102 may comprise a display screen, projector, or a printer to output the rendered computer graphics scene. The user interface output unit may comprise a binocular head mounted display device, such as a virtual reality headset. Such virtual reality headset may be capable of displaying stereoscopic images to a wearer of the headset, as is known in the art perse. Other virtual reality display systems may be employed also. Alternatively, the user interface output unit 102 may comprise a display screen such as a computer monitor or a projector. The mentioned user interface devices may also comprise external devices. In that case the system 100 does not contain the actual interface device, but rather the user interface input unit 101 and/or the user interface output unit 102 may be implemented as connectors that can communicate with the mentioned interface devices to control these external interface devices and/or receive data detected by the interface devices.

The processor 103 may comprise any suitable processor capable to control processing operations. For example, a microprocessor or a controller may be used, or a network or microprocessors or controllers. An example of such a microprocessor is an Intel Core i7 processor, manufactured by Intel Corporation. However, any suitable processor may be used. The processor 103 may comprise a plurality of microprocessors configured to cooperate with each other to divide the processing operations. The memory 104 may comprise a computer program code 105 stored thereon, which computer program code causes the processor to perform certain operations. This way, a realization of a method disclosed herein may be realized by means of such computer program code 105.

The memory 104 may comprise a volatile and/or a non-volatile memory, such as RAM, ROM, FLASH, magnetic disk, optical disk, or a combination thereof. The program code 105 may typically be stored on a non-transitory computer readable media.

The processor 103 may be configured to control the operations of the user interface input unit 101, the user interface output unit 102, the communication unit 106, the input unit 110, and memory 104. Moreover, other components (not shown) may be controlled by the processor. For example, the processor 103 may be configured to control operation of any plant scanning apparatus, display device, or virtual reality system.

The input unit 110 and the communication unit 106 may comprise any data communication device or interface, such as ethernet, USB, W-Fi transceiver and the like. These units may be configured to set up a wired or wireless communication connection, which may be a direct device-to-device communication connection or a network connection, for example. The input unit 110 and communication unit 106, although drawn as separate blocks in the drawing for explanation purposes, may be implemented as a single communication device. The input unit 110 may be configured to communicate with a scanning apparatus 130, for example an automated plant photography apparatus or another plant scanning device. Alternatively, the input unit 110 may be configured to communicate with a server system 120 on which the scanning data generated by a scanning apparatus is stored. The communication unit 106 may be configured to exchange several kinds of information with another system for monitoring plants, which may be similar to the system 100, denoted as peer system 140 in the drawing. Alternatively, the communication unit 106 may be configured to exchange such information with peer systems through a server 120.

The processor 103 may control the input unit 110 to receive data from e.g. the server 120 or from a camera or scanner 130. Such received data may be stored in the memory 104. For example, image data 107 containing images of plants (e.g. photographs, which may be for example in a JPEG or PNG format), pre-processed data 108 that contains pre-processed versions of the images of the plants, and plant characteristic information 109, received from the server, may be temporarily or more permanently stored in the memory 104. In certain implementations, the pre-processed data is stored on the server 120 and sent from the server 120 to the system 100 on demand. In that case, it may not be necessary to receive the (non-pre-processed) image data 107 in the system 100. This means that massive amounts of pre-processed image data may be stored on the server 120, for thousands of plants or more. It is even possible that one apparatus creates the pre-processed texture images and stores them on the server for use by one or more other systems 100, 140. It is possible that the pre-processed images may be created by a separate device, which may be similar in structure as the system 100 although not all components would be needed for such a preprocessing device. Alternatively, the system 100 creates the pre-processed data 108 based on the image data 107. As a side note, it is mentioned that texture data 108 is also a form of image data.

FIG. 2 illustrates a method of monitoring plants. The method may be implemented, for example, by programming the system 100 with a suitable computer program code 105. The method may also be implemented by a plurality of computer systems, wherein the functionality may be divided over a plurality of different computers.

In step 201, image data is received by the input unit 106. The received image data may comprise a plurality of image data associated with a plurality of plants, each image data representing an individual plant. It is possible that the same plant is scanned or photographed more than once, so that image data may be available of the same plant in different stages of development of the plant. Moreover, plant characteristic data 109 such as phenotype information, genotype information, experimental condition, and stage of development of each plant may be received and stored in the memory 104. This plant characteristic information may be more descriptive in nature compared to the image data, for example describing certain dimensions or number of branches, colors, root mass, etc.

In certain implementations, the image data may be already in a format of a computer graphics texture, so that the image data 107 and texture data 108 are the same, or both the original images 107 and the texture data 108 are already made available beforehand. In this case, the subsequent conversion into texture format is not necessary. Moreover, although in the following description, a computer graphics texture generating step 202 is described as a preprocessing step, this is not a limitation of the present disclosure. In an alternative implementation, the texture format may be generated on-the-fly at step 208, whenever a particular texture is applied to a particular computer graphics object.

In optional step 202, the received image data may be converted into computer graphics texture data. This preprocessing step prepares the image data for being smoothly displayed in a three-dimensional computer graphics rendering. Thus, at least the images that are foreseen to be displayed in a usage session may be pre-processed and the resulting texture data 108 may be stored in the memory 104.

The preprocessing step makes it possible to render large amounts of plants in a three-dimensional scene without extensive waiting times. The texture data 108 is more quickly processed by the processor 103 and by a graphics processing unit (GPU) of the user interface output unit 102 than the original image data 107. The texture data may be compressed texture data. In many texture formats, unlike in typical compression algorithms used for storing pictures, such as PNG and JPEG, the compression ratio is always the same, for example 4:1. For example, a 32 MB texture may be compressed to 8 MB texture, for a specific format of compression. This would fit four textures instead of just one, using the same amount of video memory. In certain embodiments, the compression scheme used is called 'S3 Texture Compression', specifically the 'DXT1' method. In a particular example of texture compression, for each 4×4 texel block of the texture the compressor may select two colors, A and B, that are mixed to approximate the texels in the block. For each texel in the block the proportion in which the colors are mixed to form the texel may be stored in the compressed texture data: all A, all B, two-thirds of A plus one-third of B, or two-thirds of B plus one-third of A. The 16 proportions fit in the same space as two texels, resulting in a constant reduction of 16 texels to the size of four texels. Herein, a texel is a picture element (pixel) of a texture.

In certain implementations, depending on the graphics hardware used, the preformatted compressed textures, for example in the DXT format, can be used directly in their compressed form by the GPU. Thus, it is not necessary to perform any further processing to the format after loading the texture. And since the compressed textures take up less space in memory compared to the uncompressed textures, more textures can fit in local video memory (i.e. on the graphics card which is local to the GPU, so faster to texture from) so there may be fewer per-frame texture uploads to local video memory. A suitable file format in which these textures may be stored is called DDS (DirectDraw Surface™), and it may help to deal with all the plant images which may otherwise be undesirably slow to load into the three-dimensional scene.

In step 203, the pre-processed texture data 108 is stored in the memory 104. Alternatively or additionally, the pre-processed texture data 108 is transmitted to a server 120 or to a peer system 140, so that other systems can re-use the texture data without having to compute it. Having the pre-processed texture data 108 stored in a local memory 104 of the system 100 may typically provide the best performance during the later steps 208-209.

In certain implementations, the following steps, in particular steps 206-209 are performed after all the necessary pre-processing has been performed in step 202, so that any of the images can be selected for immediate display, without waiting times induced by the pre-processing.

In step 204, the images are associated with corresponding plant characteristics 109. These plant characteristics may include phenotype information genotype information, and information about the stage of development of each plant at the time of the scanning of the image.

In this disclosure, a "plant characteristic" may relate to or represent aspects of the plant's genotype, phenotype, environmental condition, developmental stage, or any combination thereof. The term "genotype" refers to the genetic makeup of an individual or plant. The term "phenotype" refers to an individual or plant's characteristics or traits, particularly observable characteristics or traits such as, but not limited to morphological, physical, biochemical, developmental or behavioral characteristics or traits. The phenotype of an individual or plant can be formed by the expression of genes as well as environmental factors, and on interactions between gene expression and environmental factors. The term "environmental condition" refers to the combination of environmental factors to which a plant is exposed during a certain period of time, such as (experimental) treatment and/or grow factors. Experimental treatment may involve exposure of the whole or part of the plant to biotic and/or abiotic factors or compounds such as, but not limited to, drought, heat, insect pests, radiation and chemicals. Grow factors may be factors required for the plant to develop, such as nutrition, light and temperature. The term "development stage" refers to the stage of development of a plant, which in general runs from germination of the seed to senescence of the plant.

"Plant" refers herein to the whole plant, a part of a plant and/or a plant product, such as, but not limited to, leaf, fruit, flower, trunk and seed.

Step 204 may involve receiving or providing the data describing such plant characteristic information and an indication of the image data to which each piece of information belongs. The information may be received, for example, via communication unit 106, input unit 110, or user interface input unit 101. The association between images and plant characteristics may be provided by giving each plant a unique identifier, and by labeling each image and the plant characteristic data with the unique identifier and, optionally, the stage of development. Other ways of implementing the association are apparent to a person skilled in the art based on the present disclosure. This plant characteristic information 109 may be provided by storing it in the memory 104.

In step 205, plant characteristic information may optionally be aggregated and statistics may be calculated to provide statistical information of groups of the available plants. This breeding information may be displayed in any suitable form, by numbers, tables, graphs, and the like. It will be understood that this step is entirely optional. This statistical information may relate to any of the plant characteristic information, such as phenotype information and/or genotype information of the plants.

In step 206, a subset of the plants is selected. Typically, plants are selected by filtering based on plant characteristic data, such as the phenotype information, the genotype information, the stage of development of the plant at the time of scanning the plant, or the experimental condition. The selection may be automatic, for example based on a predetermined filter. For example, the system 100 may be pre-programmed to display the largest images or the most images showing the most mature plants or the most recently acquired images. Alternatively, the selection may be based on a user input received via the user interface input unit 101. Third, the selection may be received from a peer system 140, via communications unit 106, so that it is possible to visualize the same plant images on two different systems 100, 106 at the same time.

In step 207, for each selected plant in step 206, a computer graphics object is generated. This computer graphics object has a shape. The shape of the computer graphics object may be specific for each plant. In that case the shape may be based on the phenotype information, for example the height and width of the plant, or the shape may be determined based on the image data 107. Alternatively, all graphics objects representing plants may have the same shape. How to generate a three-dimensional computer graphics object is known to the person skilled in the art by itself, and may be done using Direct3D™ or OpenGL™ technology, for example. Shape information may, for example, be derived from proprietary software such as Blender™ or 3DMax™.

In step 208, the texture data of each selected plant is applied to the corresponding computer graphics object. That is, a surface of the computer graphics object is identified and a particular texture is applied to the identified surface of the computer graphics object. For example, if each leaf of a plant is modeled as a three-dimensional surface of the computer graphics object, and a photograph is made of each leaf, the pre-processed texture data corresponding to the photograph of the leaf may be applied to the surface of the leaf in the computer graphics object.

In a particular example implementation, the image data comprise a plurality of photographs of each plant taken from a plurality of different viewing directions. Possible viewing directions include: the plant seen from four orthogonal sides (called frontal, rear, left, and right), the roots of the plant seen from the same four sides, the plant seen from above, the roots seen from below. Of course, the plant may be photographed from more directions, e.g. five or more views around the plant. Alternatively, fewer photographs are made of each plant. Also, the number of available photographs does not need to be the same for each plant. Moreover, plants for which no images are available may be represented by means of a graph or a text, for example.

The computer graphics objects may have faces corresponding to the views from which photographs have been made. In the above example, a rectangular shaped computer graphics object may be created, so that the textures of each side photograph are applied to the top half of four faces around the computer graphics object, and the textures of the photographs of the roots are applied to the bottom half of four faces around the computer graphics object. The texture of the photograph of the top view of the plant may be applied to the top face of the computer graphics object. The texture of the bottom view of the roots of the plant, if available, may be applied to the bottom face of the computer graphics object. An example of this is illustrated in FIG. 3A and FIG. 3B.

Figure 3A:
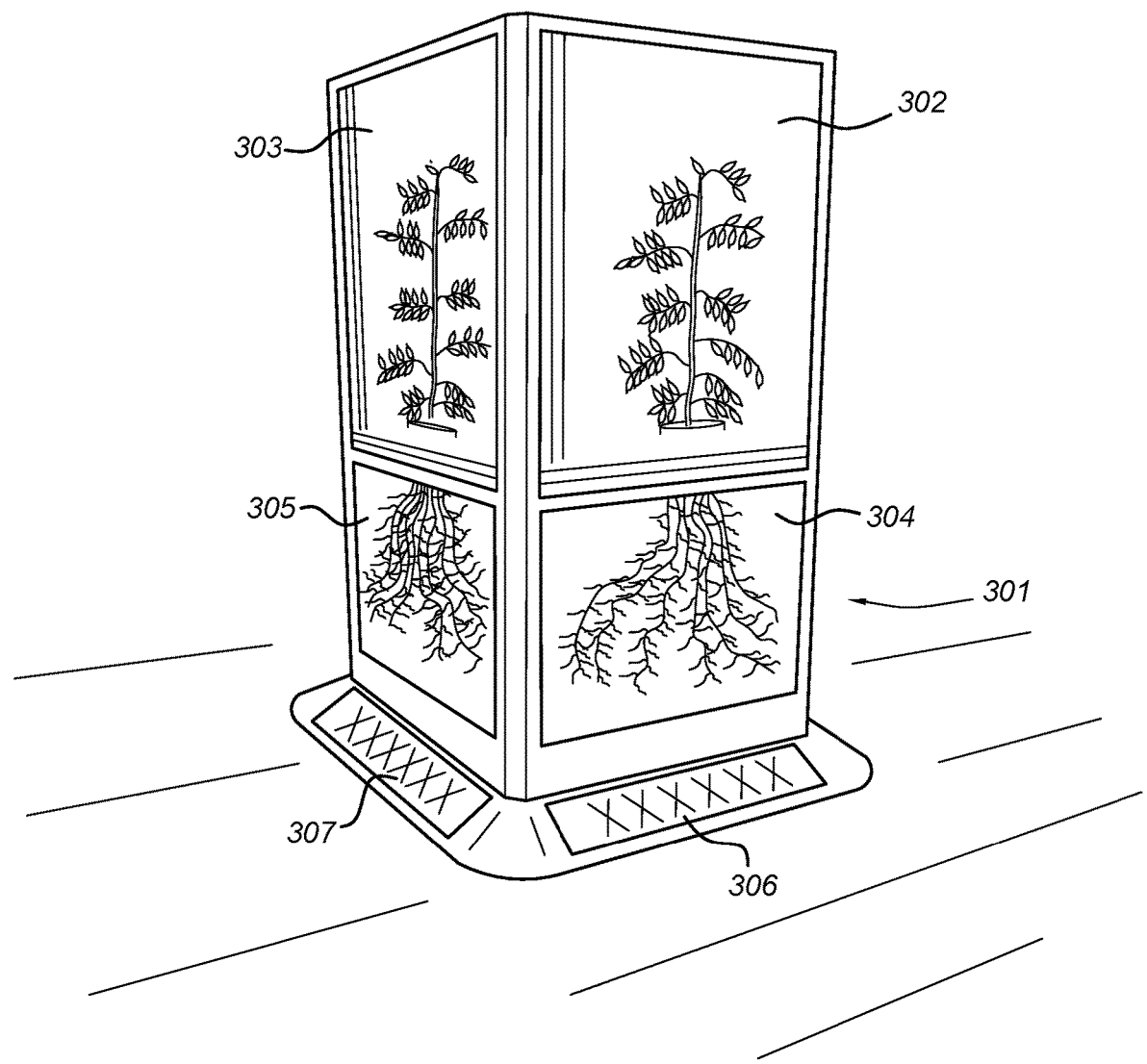
FIGS. 3A and 3B show a computer graphics object.
Figure 3B:
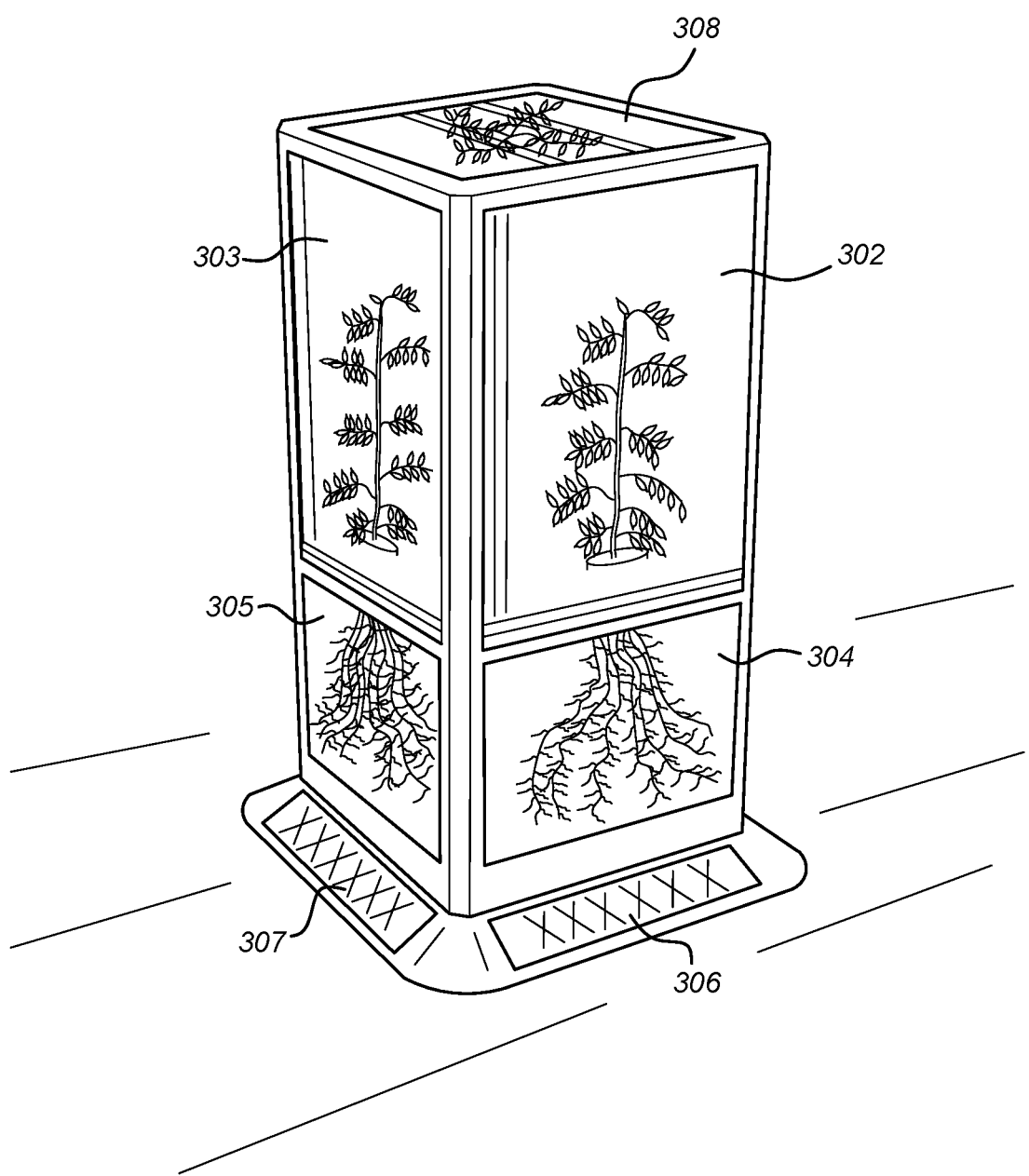

FIG. 3A shows a computer graphics rendering of a computer graphics object 301 representing a plant. The object comprises a label 306, 307 at the bottom of the object, images of the roots 304, 305 from different sides of the plant above the label 306, 307, and images of the plant 302, 303 taken from the same direction as the root images 304, 305 immediately below the plant images 302, 303. FIG. 3B shows the same computer graphics object, from a slightly different viewing angle, so that the top face showing the top image 308 is also visible in the computer graphics rendering.

Figure 4:
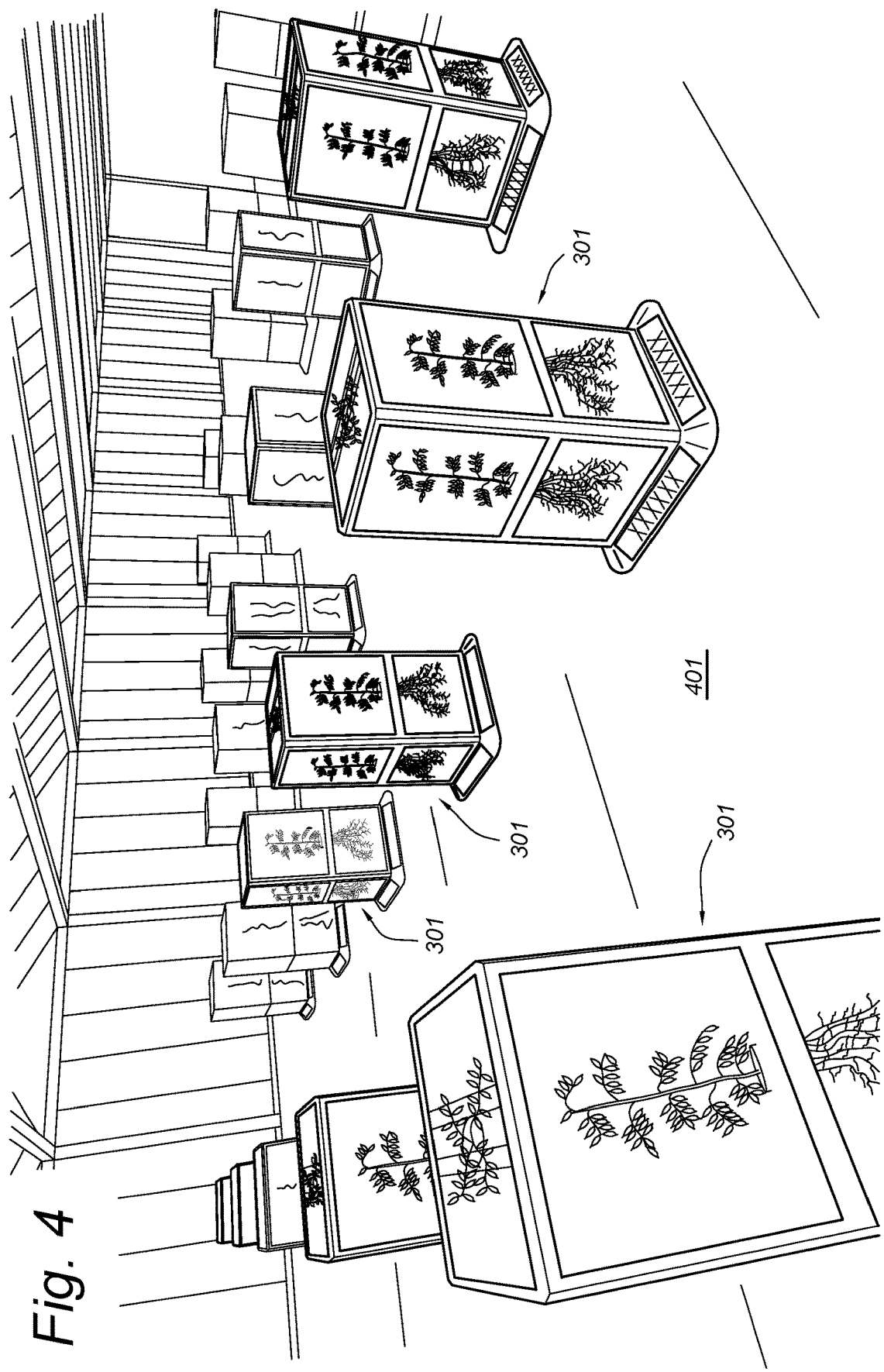
FIG. 4 shows a plurality of computer graphics objects.
Figure 5:
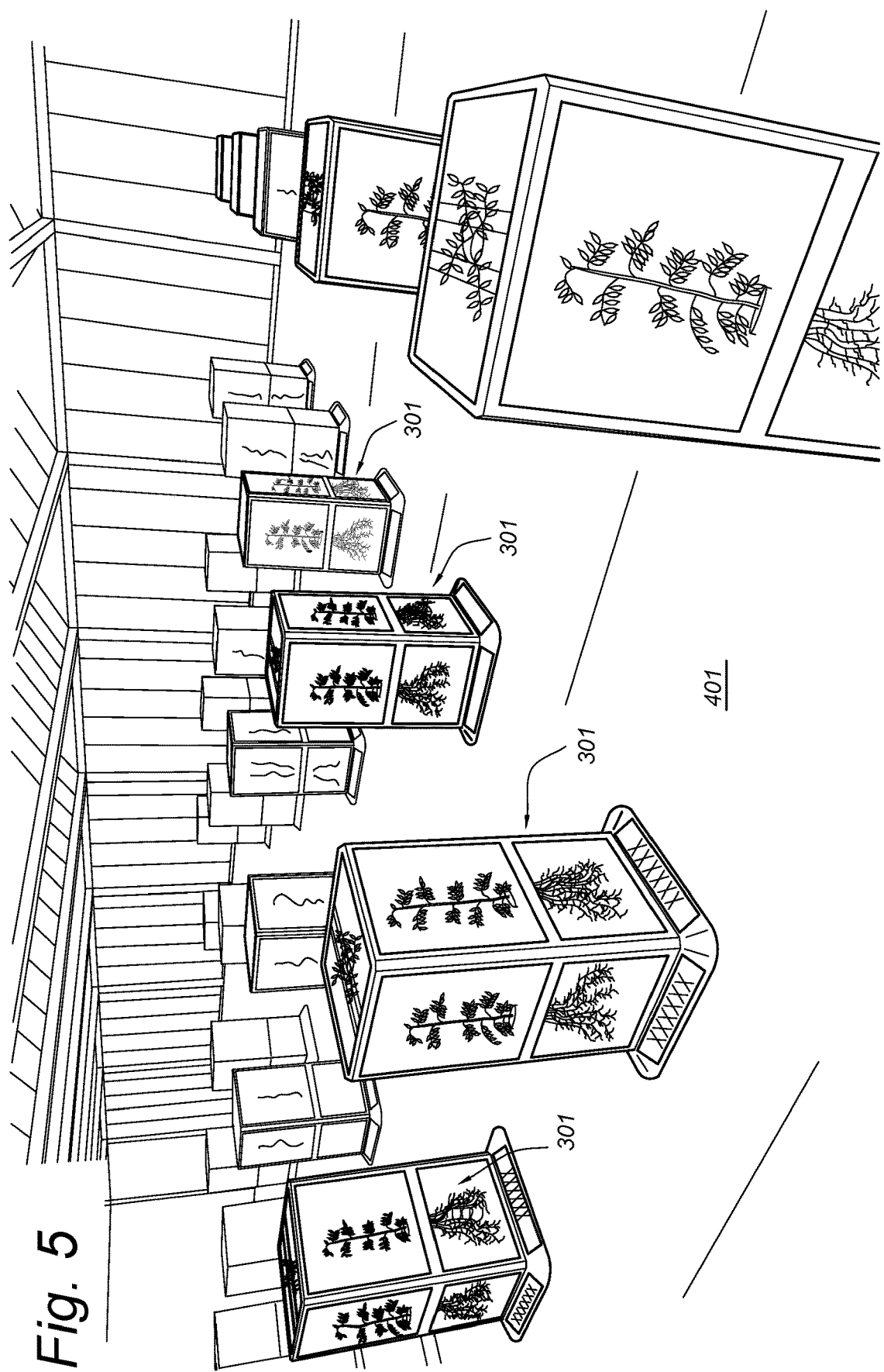
FIG. 5 shows a plurality of computer graphics objects.

In step 209, a position is assigned to each computer graphics object in the three-dimensional space of the computer graphics scene. For example, the computer graphics objects may be arranged in a rectangular grid, mimicking the layout of a greenhouse. An example of this is shown in FIG. 4. FIG. 4 shows a large number of computer graphics objects 301, arranged in a rectangular grid 401. FIG. 5 shows a similar picture using a slightly different viewing angle.

In the example shown in FIG. 4 and FIG. 5, the plants are distributed on a horizontal plane in a grid arrangement in the computer graphics scene. Other arrangements are also possible, for example in a circle in a horizontal plane, a grid arrangement in a vertical plane, or in a three-dimensional grid arrangement. Alternatively, the positions may be determined pseudo-randomly.

In certain implementations, the computer graphics objects are arranged in a predetermined order. For example, the plants may be ordered by height of the plant from short to long. When the grid is in a plane positions may be characterized by two parameters (x, y). Position (0, 0) may be for the shortest plant, the next shortest plant may be positioned at position (0, 1), and so forth, until position (0, N), wherein N is the number of plants in a row, and the next shortest plant may be positioned at position (1, 0), the next shortest plant at position (1, 1), and so forth.

Alternatively, two different characteristics may be sorted on two different axes in the grid. For example, the position on the x-axis may be determined by a height of the plant and the position on the y-axis may be determined by a weight of the plant.

Also, the position on the x-axis may be determined by some characteristic of the plant, and on the different positions on the y-axis, a number of different plants having the same characteristic may be displayed for comparison.

A fourth possible axis is a time axis; a sequence of scenes may be created, rendered, and displayed successively to create a moving three-dimensional world. The time axis of this moving world may correspond, for example, to increasing stages of development of the plants.

In step 210, a computer graphics rendering of the scene is created using, for example, the Direct3D™ or OpenGL™ engine. Alternatively, the rendering may be created by using a suitable ray-casting technique. Such rendering techniques are known to the person skilled in the art. The rendering step may result in a two-dimensional bitmap image, which can be displayed or printed, such as for example the image shown in FIG. 4. The rendering involves setting a viewing direction and viewing parameters (such as, perspective or parallel projection, resolution of the computed two-dimensional bitmap image, whether a single bitmap image or a stereoscopic image is created). Such parameters may be set according to need.

In step 211, the computer graphics rendering is output by a user interface output unit 102, such as an electronic display device, a computer monitor, a digital projector, or a virtual reality headset, for example.

The selection of a subset of the plants in step 206 may be based on an input filter defining certain selection criteria. The selection of the filter may be automatic, using a pre-programmed filter, or based on a user input.

Figure 6:
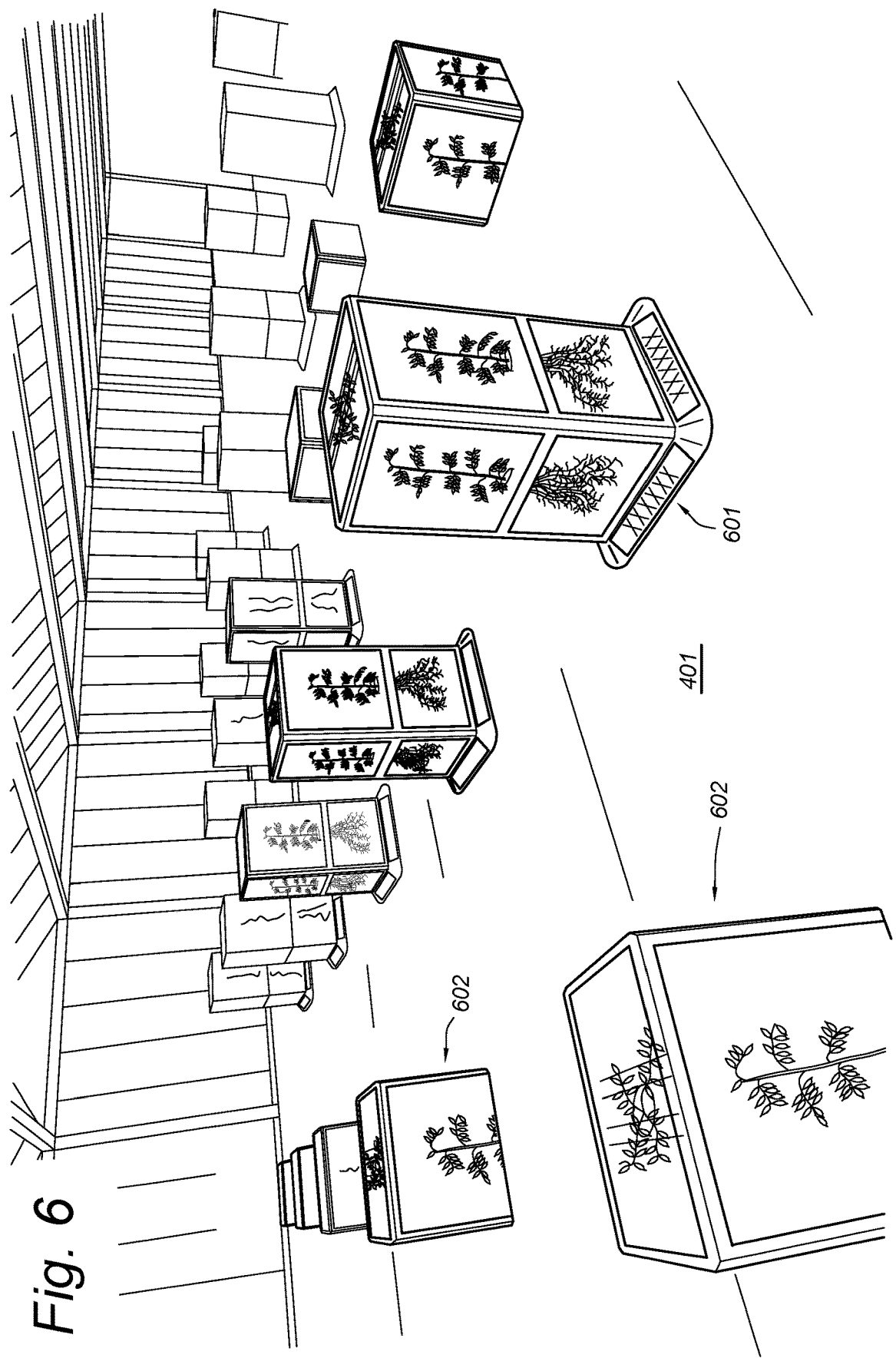
FIG. 6 shows a plurality of computer graphics objects, some of which are partly hidden.

FIG. 6 shows another example. The processor 103 may be configured to position objects 601, 602 in step 209 with different heights. This way it is possible that some of the objects (e.g. 602) are partially occluded by another, planar, object (e.g. the floor), whereas other objects (e.g. 601) are fully visible. This effect, or another visual effect, may be used to show plants satisfying certain first criteria in a first rendering mode while showing plants satisfying certain second criteria in a second rendering mode, which differs from the first rendering mode.

Figure 7:
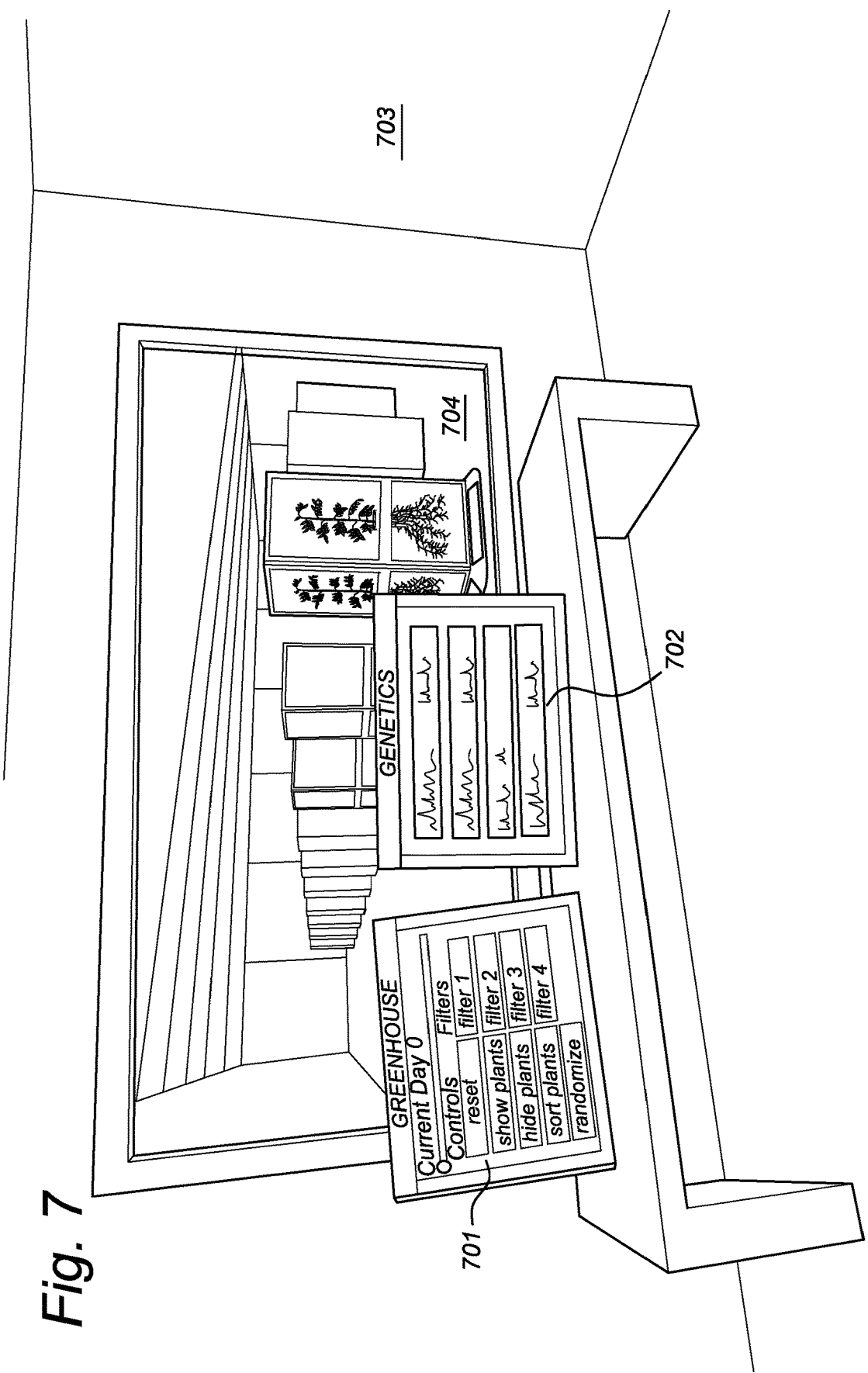
FIG. 7 shows a control panel displayed in a three-dimensional scene.

FIG. 7 shows an example of a rendering of a three-dimensional computer graphics scene comprising a user interface object 701. The user interface object 701 can comprise one or more sliders and/or buttons to set certain parameters. These parameters may select the filter, or search mask, that is applied when selecting the plants in step 206. The scene shown in FIG. 7 also contains an object 702 on which plant characteristics are displayed. The scene also contains plant objects 704, as well as an object 703, visualized as a wall, on which further plant characteristics and statistics thereof are displayed.

As a possible extension of the system disclosed above, at least some steps of the process of FIG. 2 may be performed repeatedly during an inspection session performed by a user. For example, when the computer graphics objects have been set and their textures applied and the positions set, the step of rendering the computer graphics scene 210 and outputting the computer graphics rendering 211 may be repeated. In between the repetitions, the viewing position or viewing angle may be changed. For example, the user interface input unit 101 may be configured to receive a user input while the rendering is displayed. The processor 103 may be configured to, in response to the user input, adapt a viewing position or a viewing angle of the observer based on the user input. Next, the scene may be rendered and displayed again, using the new viewing position and viewing angle. This may allow a user to virtually walk through the scene as if it were a real greenhouse.

In another possible extension of the system, the processor may be further configured to control, in relation to step 206, exchanging information about the selection of the subset of the plants with a server 120 or another system 140 for monitoring plants, using the communication unit 106. For example, information indicative of the subset may be received and used in the subsequent steps 207-211. Alternatively, the selection may be controlled by the system 100 in step 206, and the processor 103 may be configured to send information indicative of the selected subset of plants to the server 120 or peer system 140, so that they can use the same selection, enabling third parties to see the same selection of plants as displayed by the system 100. Also, the position and/or the sorting options may be exchanged with the server 120 or peer system 140. Thus, the selection of the plants and the three-dimensional positions of the computer graphic objects 301 may be synchronized with the server 120 or the other system 140 for monitoring plants.

In another possible extension of the system, the processor 103 is further configured to control transmitting and receiving information about the viewing position or viewing direction used for creating the computer graphics rendering with the server or the other system for monitoring plants. This way, it is possible that remotely located users can see each other in the computer graphics scene showing the virtual greenhouse. The processor 103 can control creating a computer graphics object representing another user and assigning a position to the computer graphic object representing the other user in the computer graphics scene based on the received information about the viewing position or viewing direction of the other user. The computer graphics object representing the other user in the computer graphics rendering of the scene.

In another possible extension of the system, breeding information including statistics of the plant characteristic data is displayed within the computer graphics scene. A computer graphics object 602 or 603 is created, which may contain, for example, text or graphs or numbers, representing breeding information, wherein the breeding information comprises statistics of the plant characteristic data. The computer graphics object 602 or 603 representing the breeding information is given a position in the computer graphics scene. Thus, the object showing the breeding information is included in the computer graphics rendering performed in step 210.

Optionally, the displayed breeding information can be coupled to the selection and/or positioning of the plants in the virtual greenhouse scene. For example, the processor 103 is configured to control retrieve the breeding information to be displayed 602, 603 from a server program. The application program may have an application program interface. The filter and sorting options may be included in the request. For example, these options are set according to a user input received via the user interface input unit 101. The server program may return statistics of the plants satisfying the filter options. The processor 103 may be configured to display the statistics, for example as a graphics object 602, 603. At the same time, in step 206, the processor 103 may select the plants using the same filter options used for the request. The position of the graphics objects in step 209 may be based on an order of the plants defined by the request. The request may, for example, have the form of a URL. The URL or the selection criteria of the request may be set by a user by interacting with the control panel 701, for example.

In the following, a few specific examples of possible requests are given in form of URL's. The format used in these examples may work with a particular server application. However, both the form and the contents are only disclosed by means of example. The examples do not limit the scope of protection. An example request in form of URL is the following:
http://localhost/graph?dataset=Side&graph=average&trait=totaldetectedarea&coloraggregation=genotype&filter=genotype=t3p,t5p,t6p
In this example request, the protocol used is hypertext transfer protocol (http), the host of the server program is the local hardware of the system 100 (localhost), the type display requested is a graph based on data from a dataset named "Side". A so-called 'average graph' is requested, using trait "total detected area" and colored by genotype. Moreover, the request specifies a filter by genotype, selecting only plants with genotype "3", "5", or "6". Thus, only the plants with genotype "3", "5", or "6" will be shown as computer graphics objects in the scene.

Another example request is the following:
http://localhost/graph?dataset=Side&graph=average&trait=mean_intensity_h&coloraggregation=genotype&filter=genotype=t1p,t5p
In this example request, again, http is used for localhost to obtain an average graph of a dataset called "Side", with the traits mean_intensity_h, colored by genotype, while filtering genotype "1" and "5". Thus, only the plants with genotype "1" or "5" will be shown as computer graphics objects in the scene.

Another example request is the following:
http://localhost/graph?dataset=Side&graph=average&trait=perimeter&coloraggregation=genotype&filter=genotype=t2p,t7p
In this example request, again, http is used for localhost to obtain an average graph of a dataset called "Side", this time with the traits "perimeter", colored by genotype, while filtering genotype "2" and "7". Thus, only the plants with genotype "2" or "7" will be shown as computer graphics objects in the scene.

http://localhost/graph?dataset=Side&graph=average&trait=height& coloraggregation=genotype&filter=genotype=t4p,t5p
In this example request, again, http is used for localhost to obtain an average graph of a dataset called "Side", this time with the traits "height", colored by genotype, while filtering genotype "4" and "5". Thus, only the plants with genotype "4" or "5" will be shown as computer graphics objects in the scene.

A method of monitoring plants may comprise providing (201) image data for a plurality of plants, each image data being associated with an individual plant, associating (204) the image data of each plant with corresponding plant characteristic data, selecting (206) a subset of the plants based on the plant characteristic data, generating (207) a plurality of computer graphics objects corresponding to the selected plants, applying (208) the image data of each selected plant in form of a computer graphics texture to the corresponding computer graphics object, determining (209) a position of each computer graphics object in a three-dimensional space of a computer graphics scene, creating (210) a computer graphics rendering of the scene, and displaying (211) the computer graphics rendering. The method may be implemented in form of a computer program product stored on a non-transitory computer readable media.

Some or all aspects of the invention may be suitable for being implemented in form of software, in particular a computer program product. The computer program product may comprise a computer program stored on a non-transitory computer-readable media. Also, the computer program may be represented by a signal, such as an optic signal or an electro-magnetic signal, carried by a transmission medium such as an optic fiber cable or the air. The computer program may partly or entirely have the form of source code, object code, or pseudo code, suitable for being executed by a computer system. For example, the code may be executable by one or more processors.

The examples and embodiments described herein serve to illustrate rather than limit the invention. The person skilled in the art will be able to design alternative embodiments without departing from the spirit and scope of the present disclosure, as defined by the appended claims and their equivalents. Reference signs placed in parentheses in the claims shall not be interpreted to limit the scope of the claims. Items described as separate entities in the claims or the description may be implemented as a single hardware or software item combining the features of the items described.

The invention claimed is:

1. A system for monitoring plants, comprising
an input unit for receiving image data;
a processor configured to control:
provding image data for a plurality of plants, each image data being associated with an individual plant;
associating the image data of each plant with corresponding plant characteristic data,
selecting a subset of the plants based on the plant characteristic data,
generating a plurality of computer graphics objects corresponding to the selected plants, wherein each computer graphics object defines a shape having a surface,
applying the image data of each selected plant in form of a computer graphics texture to the surface of the corresponding computer graphics object,
determining a position of each computer graphics object in a three-dimensional space of a computer graphics scene, wherein the determining of the position of each computer graphics object comprises determining a position of each computer graphics object based on the plant characteristic information, and
creating a computer graphics rendering of the scene; and
an output unit for displaying the computer graphics rendering.

2. The system of claim 1, wherein the plant characteristic information of a plant comprises information about at least one of a phenotype of the plant, a genotype of the plant, a stage of development of the plant, and an experimental condition to which the plant was exposed.

3. The system of claim 1, wherein the processor is further configured to control selecting at least one filter option based on a user input, wherein the at least one filter option defines a filter with respect to the plant characteristic data; wherein the selecting the subset of the plants is further based on the filter option.

4. The system of claim 1, wherein the processor is further configured to control selecting at least one sorting option based on a user input, wherein the at least one sorting option defines an order of the plants with respect to the plant characteristic information, wherein the three-dimensional position of each computer graphics object is further based on the defined order of the plants.

5. The system of claim 1, wherein the processor is configured to control providing pre-processed computer graphics texture data for each of the plurality of plants before selecting the subset of the plants, wherein the computer graphics texture data is in a texture compressed form.

6. The system of claim 5, wherein the providing pre-processed computer graphics texture data comprises providing a plurality of versions of the texture data at different scales.

7. The system of claim 1, wherein the image data comprise a plurality of photographs of an individual plant taken from a plurality of different viewing angles, and wherein the computer graphics objects have faces corresponding to the plurality of different viewing angles, and wherein the computer graphics texture corresponding to a photographic image is applied to the corresponding face of the computer graphics object.

8. The system of claim 1, wherein the creating a computer graphics rendering comprises:
creating a stereoscopic computer graphics rendering for a binocular viewing device.

9. The system of claim 1, further comprising:
a user interface input unit for receiving a user input, and
wherein the processor is further configured to control adapting a viewing position or a viewing angle of the observer based on the user input received through the user interface device, the viewing position or viewing angle being used for the creating the computer graphics rendering.

10. The system of claim 1, wherein the processor is further configured to control
exchanging information about the selection of the subset of the plants with a server or another system for monitoring plants, and
synchronizing the selection of the plants and the three-dimensional positions of the computer graphic objects with the server or the other system for monitoring plants.

11. The system of claim 10, wherein the processor is further configured to control
transmitting and receiving information about the viewing position or viewing direction used for creating the computer graphics rendering with the server or the other system for monitoring plants, and
creating a computer graphics object representing another user and assigning a position to the computer graphic object representing the other user in the computer graphics scene based on the received information about the viewing position or viewing direction of the other user, and
including the computer graphics object representing the other user in the computer graphics rendering of the scene.

12. The system of claim 1, wherein the processor is configured to control displaying breeding information including statistics of the plant characteristic data, by generating a computer graphics object representing breeding information, wherein the breeding information comprises statistics of the plant characteristic data, associating the computer graphics object representing the breeding information with a position in the computer graphics scene, and including the computer graphics object representing the breeding information in the computer graphics rendering of the scene.

13. The system of claim 12, wherein the processor is configured to control
retrieving the breeding information to be displayed from a server program by submitting a request to an application program interface, wherein the request is indicative of at least one filter option and/or sorting option with respect to the plant characteristic data,
wherein the selecting the subset of the plants is performed based on the filter option indicated by the request or the determining the position of each computer graphics object is performed based on the sorting option indicated by the request.

14. A method of monitoring plants, comprising
providing image data for a plurality of plants, each image data being associated with an individual plant;
associating the image data of each plant with corresponding plant characteristic data;
selecting a subset of the plants based on the plant characteristic data,
generating a plurality of computer graphics objects corresponding to the selected plants, wherein each computer graphics object defines a shape having a surface;
applying the image data of each selected plant in form of a computer graphics texture to the surface of the corresponding computer graphics object;
determining a position of each computer graphics object in a three-dimensional space of a computer graphics scene, wherein the determining of the position of each computer graphics object comprises determining a position of each computer graphics object based on the plant characteristic information;
creating a computer graphics rendering of the scene; and
displaying the computer graphics rendering.

15. A non-transitory storage media storing instructions for causing a computer system to perform the method of claim 14.

* * * * *